(12) United States Patent
Gresham

(10) Patent No.: US 7,329,233 B2
(45) Date of Patent: Feb. 12, 2008

(54) SURGICAL SYSTEM FOR LAPAROSCOPIC SURGERY

(75) Inventor: Richard D. Gresham, Guilford, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 98 days.

(21) Appl. No.: 10/958,455

(22) Filed: Oct. 5, 2004

(65) Prior Publication Data

US 2006/0074374 A1    Apr. 6, 2006

(51) Int. Cl.
*A61M 37/00* (2006.01)
*A61M 5/178* (2006.01)

(52) U.S. Cl. .............. 604/26; 604/164.01; 604/164.12

(58) Field of Classification Search ............... 604/158, 604/117, 164.01, 164.02, 164.11, 164.12, 604/104, 26, 506; 606/15, 119, 174, 185, 606/191, 198
See application file for complete search history.

(56) References Cited

U.S. PATENT DOCUMENTS

| | | | |
|---|---|---|---|
| 1,527,291 A | 7/1925 | Zorraquin | |
| 4,808,168 A | 2/1989 | Warring | |
| 4,869,717 A | 9/1989 | Adair | |
| 5,098,388 A | 3/1992 | Kulkashi et al. | |
| 5,114,407 A | 5/1992 | Burbank | |
| 5,137,509 A * | 8/1992 | Freitas | 604/26 |
| 5,139,485 A | 8/1992 | Smith et al. | |
| 5,183,464 A | 2/1993 | Dubrul et al. | |
| 5,256,148 A | 10/1993 | Smith et al. | |
| 5,284,474 A | 2/1994 | Adair | |
| 5,290,276 A | 3/1994 | Sewell, Jr. | |
| 5,300,084 A | 4/1994 | Johnson | |
| 5,312,351 A | 5/1994 | Gerrone | |
| 5,320,608 A | 6/1994 | Gerrone | |

(Continued)

OTHER PUBLICATIONS

International Search Report for corresponding PCT Application No. PCT/US2004/33074 (3 pages).

*Primary Examiner*—Catherine S. Williams

(57) ABSTRACT

An insufflation apparatus includes an elongated sleeve defining a longitudinal axis and having a proximal end and a distal end with a sharpened tip, an insufflation housing connected to the proximal end of the elongated sleeve and defining a port for receipt of insufflation gases, and a stylet disposed within the elongated sleeve and defining a passageway to direct the insufflation gases from the port into a body cavity. The stylet is movable between an extended position wherein the distal end of the stylet extends beyond the sharpened tip of the elongated sleeve and a retracted position wherein the distal end of the stylet is proximal of the sharpened tip of the elongated sleeve. A biasing member may be engagable with the stylet so as to bias the stylet toward the extended position. Preferably, the housing has a translucent wall and the stylet is dimensioned so that the proximal end of the stylet is visible through the translucent wall when the stylet is in the retracted position. In one embodiment, the port of the housing includes the translucent wall. The port may be in general alignment with the longitudinal axis of the elongated sleeve, or alternatively, in transverse relation relative to the longitudinal axis of the elongated sleeve. In another embodiment, the housing includes an indicator bulb disposed so as to receive the proximal end of the stylet. The indicator bulb has the translucent wall so that the proximal end of the stylet is visible through the indicator bulb when the stylet is in the retracted position.

15 Claims, 15 Drawing Sheets

U.S. PATENT DOCUMENTS

| | | |
|---|---|---|
| 5,383,859 A | 1/1995 | Sewell, Jr. |
| 5,389,077 A | 2/1995 | Melinyshyn et al. |
| 5,421,821 A | 6/1995 | Janicki et al. |
| 5,423,760 A | 6/1995 | Yoon |
| 5,423,770 A | 6/1995 | Yoon |
| 5,431,676 A | 7/1995 | Dubrul et al. |
| 5,437,643 A | 8/1995 | Transue |
| 5,454,790 A | 10/1995 | Dubrul |
| 5,562,611 A | 10/1996 | Transue |
| 5,669,883 A | 9/1997 | Scarfone et al. |
| 5,695,462 A | 12/1997 | Sutcu et al. |
| 5,713,874 A * | 2/1998 | Ferber ............... 604/198 |
| 5,746,720 A | 5/1998 | Stouder, Jr. |
| 5,810,776 A | 9/1998 | Bacich et al. |
| 5,814,058 A | 9/1998 | Carlson et al. |
| 5,827,319 A | 10/1998 | Carlson et al. |
| 5,857,999 A * | 1/1999 | Quick et al. ............... 604/107 |
| 6,080,174 A | 6/2000 | Dubrul et al. |
| 6,156,006 A | 12/2000 | Brosens et al. |
| 6,193,692 B1 | 2/2001 | Harris et al. |
| 6,245,052 B1 | 6/2001 | Orth et al. |
| 6,293,952 B1 | 9/2001 | Brosens et al. |
| 6,325,812 B1 | 12/2001 | Dubrul et al. |
| 6,447,527 B1 | 9/2002 | Thompson et al. |
| 6,494,893 B2 | 12/2002 | Dubrul et al. |
| 6,589,225 B2 | 7/2003 | Orth et al. |
| 6,656,160 B1 | 12/2003 | Johnson et al. |

* cited by examiner

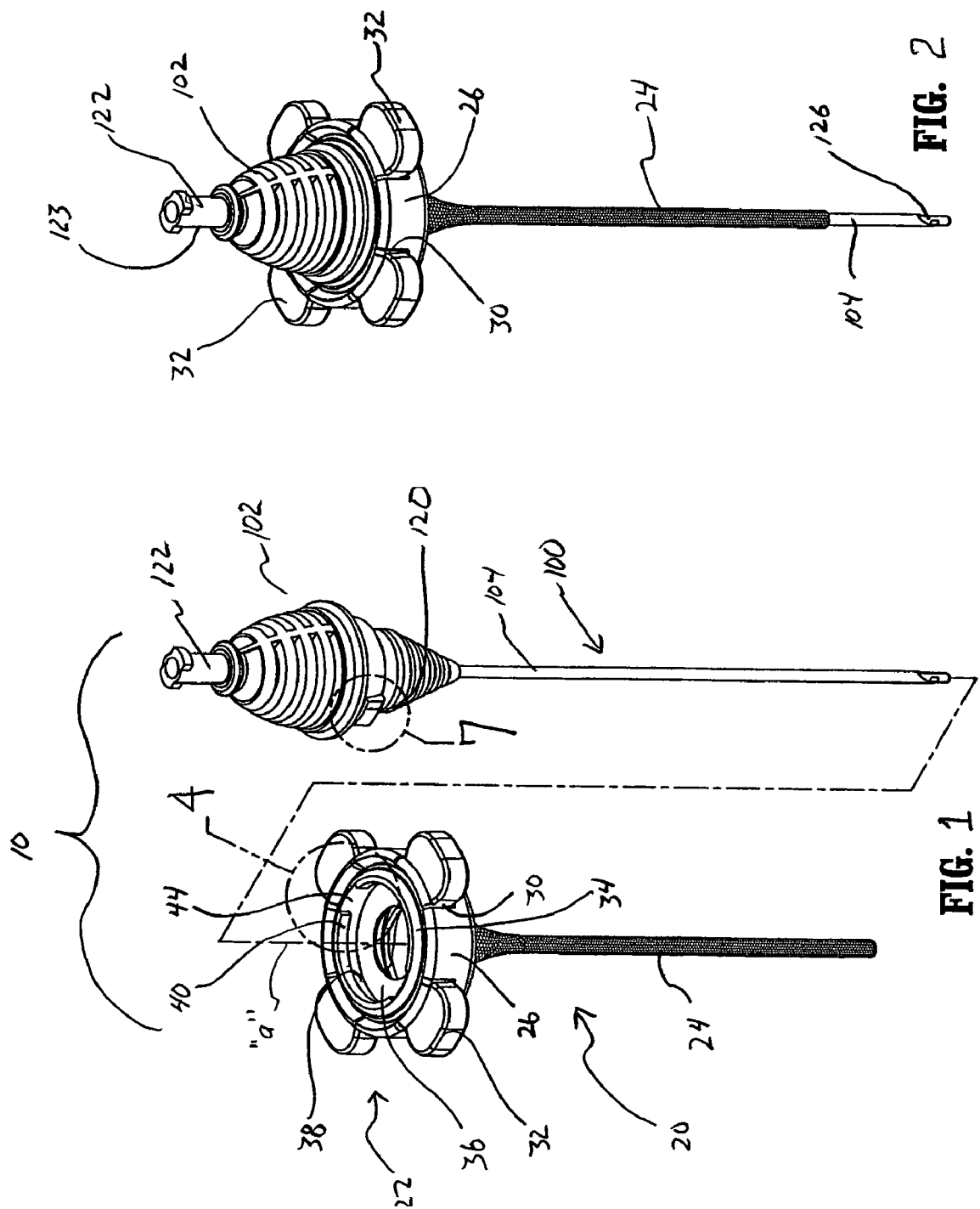

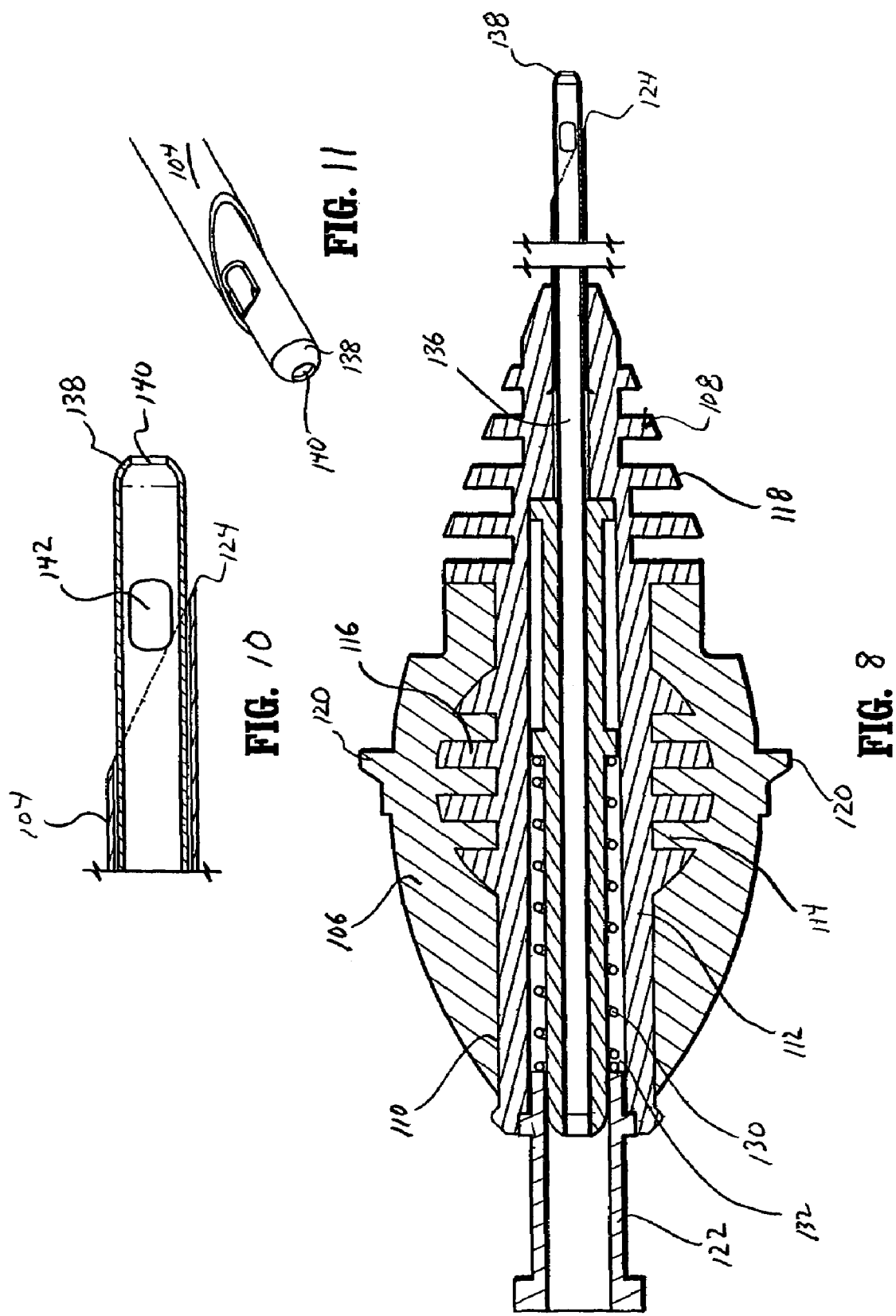

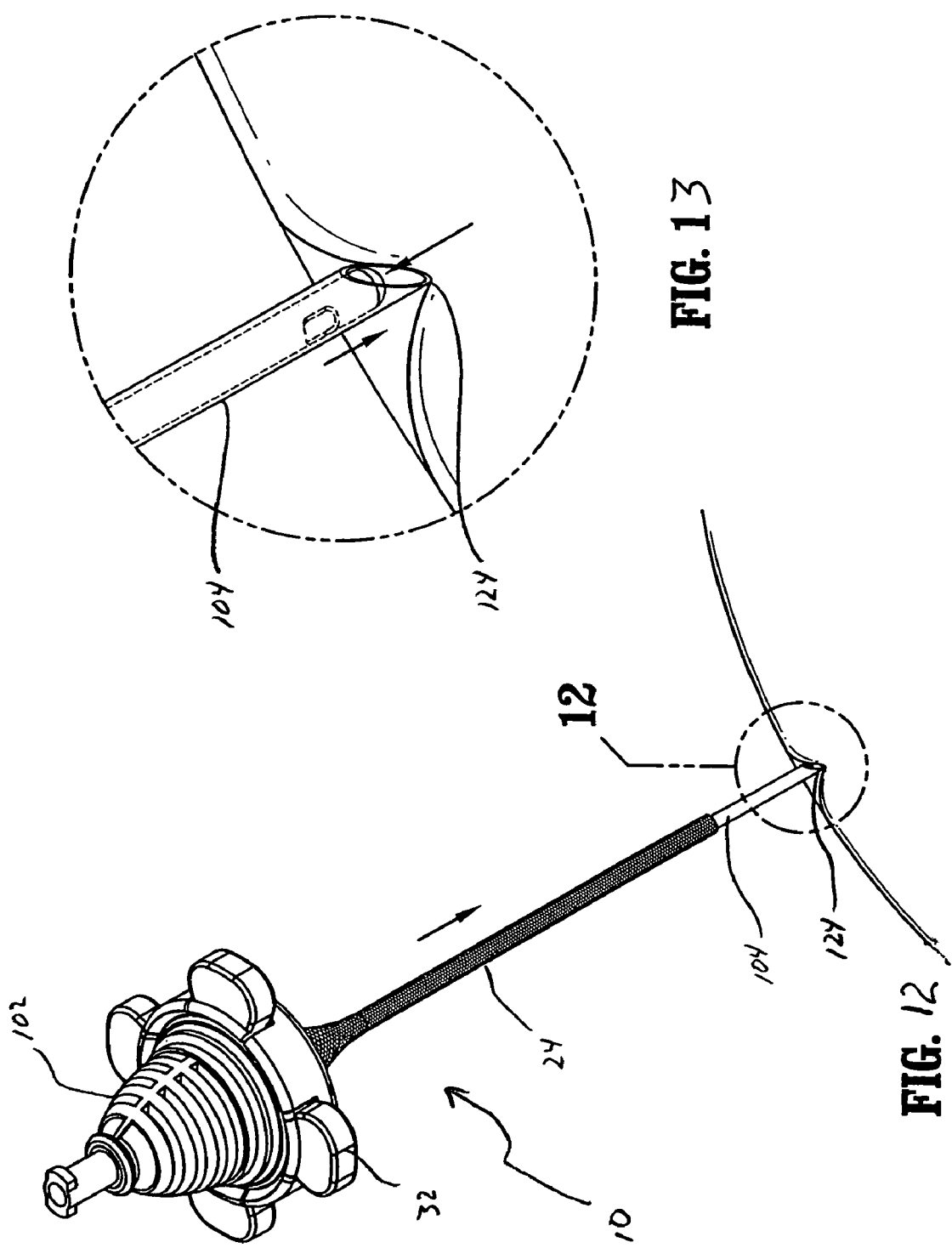

SURGICAL SYSTEM FOR LAPAROSCOPIC SURGERY

BACKGROUND

1. Field of the Disclosure

The present disclosure relates generally to a surgical system incorporating an insufflation instrument and cooperative access instrument for providing insufflation of, and direct access, to an underlying body cavity.

2. Description of the Prior Art

Minimally invasive surgical procedures involve percutaneously accessing an internal surgical site with small-diameter access tubes (typically 5 to 12 mm), usually referred to as trocars, which penetrate the skin and permit access to the desired surgical site. A viewing scope is introduced through one trocar, and the surgeon operates using instruments introduced through other appropriately placed trocars while viewing the operative site on a video monitor connected to the viewing scope. The surgeon is thus able to perform a wide variety of surgical procedures requiring only several 5 to 12 mm punctures at the surgical site. Consequently, patient trauma and recovery time are greatly reduced. Minimally invasive surgical procedures include laparoscopic procedures which involve the insufflation of the patient's abdominal region to raise the abdominal wall and create sufficient operating space to perform a desired procedure. Typically, an insufflation needle is utilized to insufflate the abdominal region.

Insufflation needles may be utilized in an access system, as well. Commonly assigned U.S. Pat. No. 5,431,676 to Dubrul et al., the contents of which are incorporated herein by reference in its entirety, discloses an access system incorporating an elongate dilation member and an expansion member receivable within an axial lumen of the trocar. The dilation member includes a tubular braid which is radially expandable from a small diameter configuration to a large diameter configuration. A removable sheath may cover the braid. In use, the dilation member is percutaneously introduced to a target site within a patient's body, e.g., within the abdomen of the patient. An insufflation needle may be assembled with the dilation member for introduction of the dilation member and insufflation of the abdomen. The expansion member is thereafter introduced within the dilation member to radially expand the tubular braid. The Dubrul '676 system has proven to be highly effective in conjunction with laparoscopic and other minimally invasive surgical procedures.

SUMMARY

Accordingly, the present disclosure relates to further improvements in laparoscopic surgery. In accordance with one embodiment of the present disclosure, an insufflation apparatus includes an elongated sleeve defining a longitudinal axis and having a proximal end and a distal end with a sharpened tip, a housing having a proximal end and a distal end, the distal end being connected to the proximal end of the elongated sleeve and defining a port for receipt of insufflation gases, and a stylet disposed within the elongated sleeve and defining a passageway to direct the insufflation gases from the port into a body cavity. The stylet is movable between an extended position wherein the distal end of the stylet extends beyond the sharpened tip of the elongated sleeve and a retracted position wherein the distal end of the stylet is proximal of the sharpened tip of the elongated sleeve. A biasing member may be engagable with the stylet so as to bias the stylet toward the extended position. Preferably, the proximal end of the housing has a translucent wall and the stylet is dimensioned so that the proximal end of the stylet is visible through the translucent wall when the stylet is in the retracted position. In one embodiment, the port of the housing includes the translucent wall. The port may be in general alignment with the longitudinal axis of the elongated sleeve, or alternatively, in transverse relation relative to the longitudinal axis of the elongated sleeve. In another embodiment, the housing includes an indicator bulb disposed so as to receive the proximal end of the stylet. The indicator bulb has the translucent wall so that the proximal end of the stylet is visible through the indicator bulb when the stylet is in the retracted position.

The stylet may define an internal lumen to permit passage of the insufflation gases therethrough and at least one opening to permit the insufflation gases to exit the internal lumen. Preferably, the stylet includes an axial opening and a second opening spaced from the axial opening. The axial opening and the second opening are adapted to permit the insufflation gases to exit the internal lumen of the stylet.

Preferably, the housing defines a flow path for the insufflation gases to flow through the port to the axial lumen of the stylet wherein the flow path is interrupted upon movement of the stylet to the retracted position to thereby prevent the insufflation gases from entering the axial lumen of the stylet. The port is disposed transversely with respect to the longitudinal axis of the elongated sleeve. The stylet is arranged within the passage so that, in the retracted position, the stylet blocks an opening within the port.

The insufflation apparatus may further include an access member dimensioned to access an underlying body cavity. The access member includes a radially expandable sleeve. The elongated sleeve and the stylet are positionable within the access member. Means for securing the access member relative to the elongated sleeve may be provided. In one embodiment, the access member includes an access housing and an access sleeve. The means for securing includes corresponding thread members disposed on the access housing and the insufflation housing. Alternatively, the means for securing includes a locking shelf and locking tab mechanism associated with the access housing and the insufflation housing.

In another preferred embodiment, an insufflation apparatus includes a housing having a distal end, a proximal end and an insufflation port for connection to a supply of insufflation gases, an elongated sleeve connected to the housing and extending distally therefrom, and having a penetrating tip, and a stylet disposed within the sleeve and being movable from an extended position to a retracted position to expose the penetrating tip of the elongated sleeve. One of the elongated sleeve and the stylet defines a passageway for passage of insufflation gases from the port into a body cavity. The proximal end of the housing has a translucent wall to permit visualization within an interior of the housing to confirm movement of the stylet to the retracted position. In one preferred embodiment, the insufflation port of the housing defines the translucent wall. In another embodiment, the insufflation housing includes an indicator bulb. The indicator bulb defines the translucent wall.

A method for performing a surgical procedure is provided. The method comprises the steps of: providing an insufflation apparatus including an insufflation housing, an elongated sleeve defining a longitudinal axis and having a penetrating end, and a stylet disposed within the elongated sleeve and defining a passageway for passage of insufflation gases;

positioning the insufflation apparatus against the body of a patient such that the stylet moves from an extended position to a retracted position to expose the penetrating distal end of the elongated sleeve; visually verifying that the stylet is in the retracted position by viewing the interior of the insufflation housing through a transparent wall portion of the insufflation housing; advancing the penetrating end through tissue to access an underlying body cavity; and introducing insufflation gases into the passageway of the stylet to insufflate the body cavity.

BRIEF DESCRIPTION OF THE DRAWINGS

Embodiments of the present disclosure will be better appreciated by reference to the drawings wherein:

FIG. 1 is a perspective view of the access system in accordance with the principles of the present disclosure illustrating the insufflation instrument and the access instrument of the system in a disassembled condition;

FIG. 2 is a perspective view of the access system in accordance with the embodiment of FIG. 1 illustrating the insufflation instrument and the access instrument in an assembled condition;

FIG. 8 is a side cross-sectional view of the insufflation instrument in accordance with the embodiment of FIGS. 1-7 illustrating the stylet of the insufflation instrument in an extended position;

FIG. 10 is an enlarged sectional view of the distal end of the insufflation instrument in accordance with the embodiment of FIGS. 1-9;

FIG. 11 is an enlarged perspective view of the distal end of the insufflation instrument in accordance with the embodiment of FIGS. 1-10;

FIGS. 12 and 13 are perspective views illustrating insertion of the surgical system into body tissue;

DETAILED DESCRIPTION OF THE PREFERRED EMBODIMENTS

Figure 3:
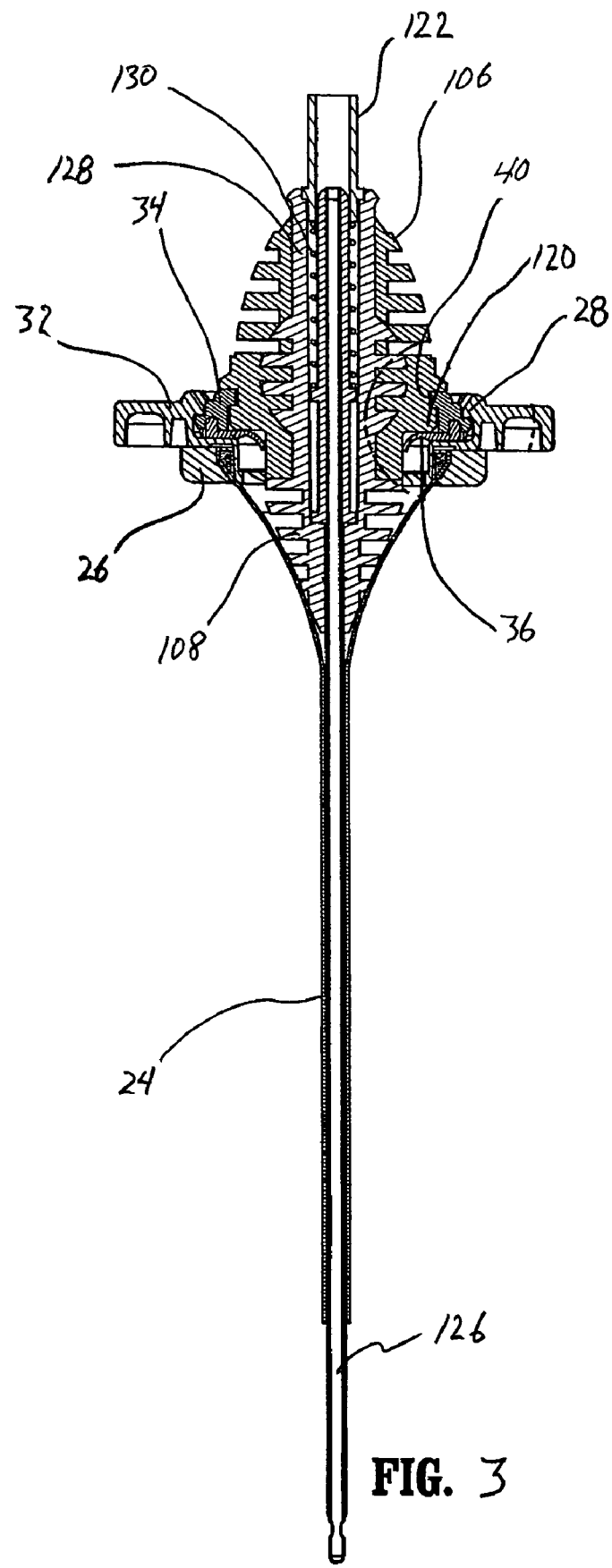
FIG. 3 is a side cross-sectional view of the assembled access system in accordance with the embodiment of FIGS. 1 and 2.

The principles of the present disclosure are applicable to a variety of surgical systems adapted for permitting percutaneous access to a target site. These systems include, but are not limited to, trocars and/or cannulas, catheters, hand access devices, scopes, etc. The present disclosure is contemplated for use in various surgical procedures including, e.g., laparoscopic, arthroscopic, thoracic, etc.

In the following description, as is traditional, the term "proximal" will refer to the portion of the instrument closest to the operator while the term "distal" refers to the portion of the instrument most remote from the operator.

Referring now to the drawings wherein like reference numerals identify similar or like elements throughout the several views, FIGS. 1-2 illustrate the novel surgical system for insufflating and permitting access to an underlying body cavity in accordance with the principles of the present disclosure. Surgical system 10 generally includes an access instrument 20 and an insufflation instrument 100 which is at least partially positionable within the access instrument 10. Access instrument 20 provides access through tissue and into an underlying body cavity, e.g., the abdominal or peritoneal cavity. Insufflation instrument 100 is used to introduce insufflation gases into the body cavity to expand the cavity to facilitate access to the organs and tissue therein.

Access instrument 20 is generally disclosed in commonly assigned Provisional Application Ser. No. 60/512,548, filed Oct. 17, 2003, the entire contents of which are incorporated herein by reference. Thus, reference may be made to the '548 application for specific details of the components of access instrument 20. Generally, however, access instrument 20 includes access housing 22 and elongate member 24 extending from the access housing 22. Access housing 22 and elongate member 24 define a longitudinal axis "a" which extends through and along the length of access instrument 20. As best seen in FIG. 1, access housing 22 includes several components, which, when assembled, define a structure advantageously dimensioned to be held by the surgeon. Access housing 22 has a base 26 and a hub 28 which at least partially resides within the base 26. Base 26 defines a plurality of recesses 30 radially displaced relative to longitudinal axis "a". Recesses 30 are generally rectangular in configuration as shown. Hub 28 has a plurality of vertical locks or tabs 32 which are received within correspondingly positioned and dimensioned recesses 30 of base 26 in the assembled condition of access housing 22. Alternatively, access housing 22 may be formed monolithically to define a single component.

Figure 4:
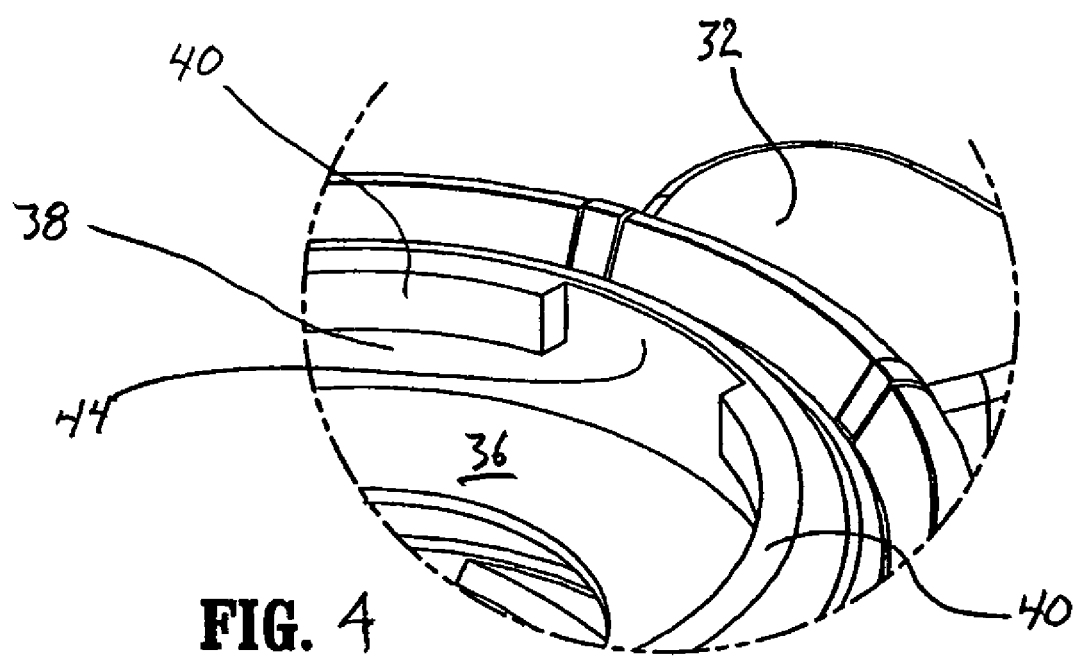
FIG. 4 is an enlarged perspective view of the access housing of the access instrument as indicated on FIG. 1.

Access housing 22 desirably includes cover 34 that encloses the hub 28 and a seal 36 within base 26. Cover 34 defines annular wall 38. As best depicted in FIG. 4, annular wall 38 has a pair of internal ledges or locking shelves 40. Shelves 40 are semicircular in shape and are separated by gaps 44. Shelves 40 serve to secure insufflation instrument 100 within access instrument 20 as will be discussed. The cover 34, hub 28 and/or base 26 may be arranged to snap together, adhered together, or welded.

Seal 36 is adapted to permit passage of an object, e.g., an insufflation instrument 100, a surgical instrument, guide wire, catheter or the hand of a surgeon in sealed relation therewith. The seal may be fabricated from an elastomeric material and may have a layer of fabric mounted or embedded therein. Such arrangement is disclosed in certain embodiments of commonly assigned U.S. Pat. No. 6,702,787 to Racenet, the contents of which are incorporated herein by reference. In the preferred embodiment, seal 36 is a septum seal defining a central aperture which expands to form a seal about the instrument. Other valve or seal types are also contemplated including zero-closure valves, slit valves, septum valves, double slit valves, an inflatable bladder, flapper or gel valve arrangements, etc.

The components of access housing 22 may be fabricated from any suitable generally rigid material (not withstanding the seal) including stainless steel, titanium or a rigid polymeric material.

Referring to FIGS. 1-3, elongate member 24 of access instrument 20 is connected to access housing 22. Elongate member 24 defines a generally tubular shape as shown. Elongate member 24 may be fabricated from any material which is capable of receiving inflation instrument 100, and/or a cannula, dilator, or an endoscopic or laparoscopic surgical instrument. The materials are desirably medical grade materials including polymers and metals, and may include one or more membranes and/or filaments. In an exemplary embodiment, elongate member 24 includes a braided material of elastic or inelastic filaments covered by an elastomeric membrane of, e.g., urethane, or any elastomeric material or as generally disclosed in certain embodiments of commonly assigned U.S. Pat. Nos. 5,431,676 and 6,245,052, the entire contents of each being incorporated herein by reference. It is also envisioned that a polyethylene sheath may be assembled over elongate member 24. Elongate member 24 may comprise an elastomeric member or members without the braided material. Embodiments may include a material incorporating filaments, where the filaments may be elastic, inelastic, monofilaments, multifilaments, braided, woven, knitted or non-woven materials. Elongate member 24 may comprise a braided, woven, knitted or non-woven material with or without an elastomeric membrane. In a preferred embodiment, elongate member 24 is in the form of a tubular braid which is expandable from a small diameter configuration to a large diameter configuration upon insertion of a dilator therein as disclosed in the aforementioned '676 and '052 patents. Other arrangements for elongated member are also envisioned. For example, elongate member 24 may be a rigid cannula or trocar sleeve, or alternatively, may be flexible and fabricated from an elastomeric material.

Access instrument 20 is assembled such that elongate member 24 is attached to access housing 22. Elongate member 24 is captured between base 26 and hub 28, in the embodiment shown in FIG. 3. In further embodiments, access housing 22 may comprise a monolithically formed component to which the elongate member 24 is secured by welding or using adhesives.

Referring now to FIGS. 5-8, in conjunction with FIGS. 1-3, insufflation instrument 100 will be discussed. Insufflation instrument 100 includes housing 102 and insufflation sleeve 104 extending distally from the housing 102. Housing 102 includes first and second housing components 106, 108 connected to each other through conventional means including cements, adhesives, snap-fit etc. In one preferred arrangement best depicted in FIG. 8, first component 106 has an enlarged axial bore 110. Second component 108 includes extension 112 which is received within axial bore 110 in the assembled condition of first and second components 106, 108. First and second components 106, 108 may further include respective internal ribs 114, 116 to further facilitate securement of the two components.

Figure 7:
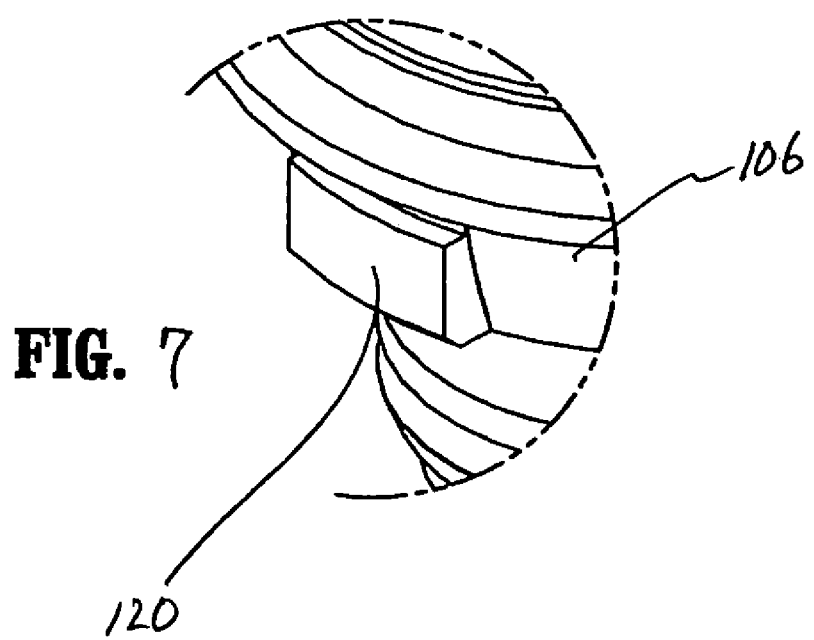
FIG. 7 is an enlarged perspective view of the insufflation housing of the insufflation instrument as indicated on FIG. 1.
Figure 5:
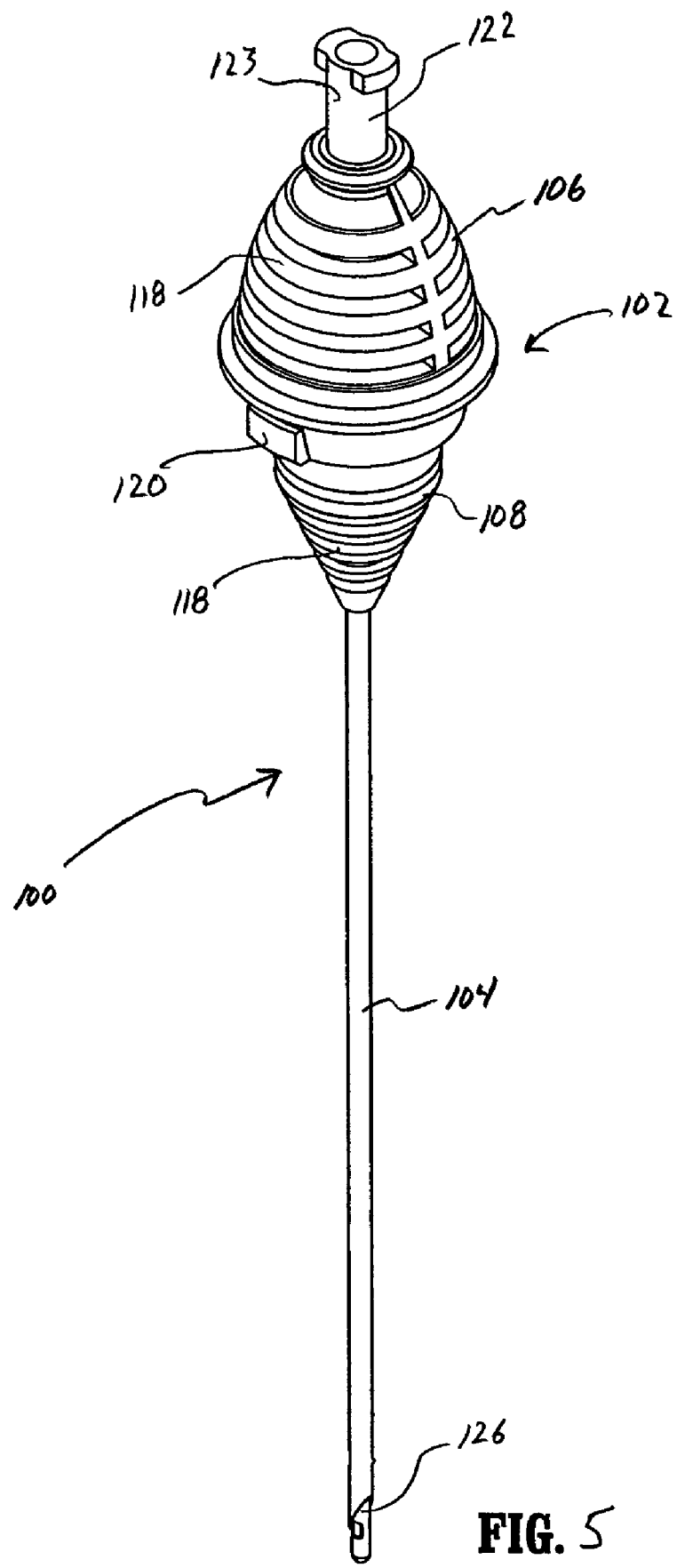
FIG. 5 is a perspective view of the insufflation instrument of the access system in accordance with the embodiment of FIGS. 1-4.
Figure 6:
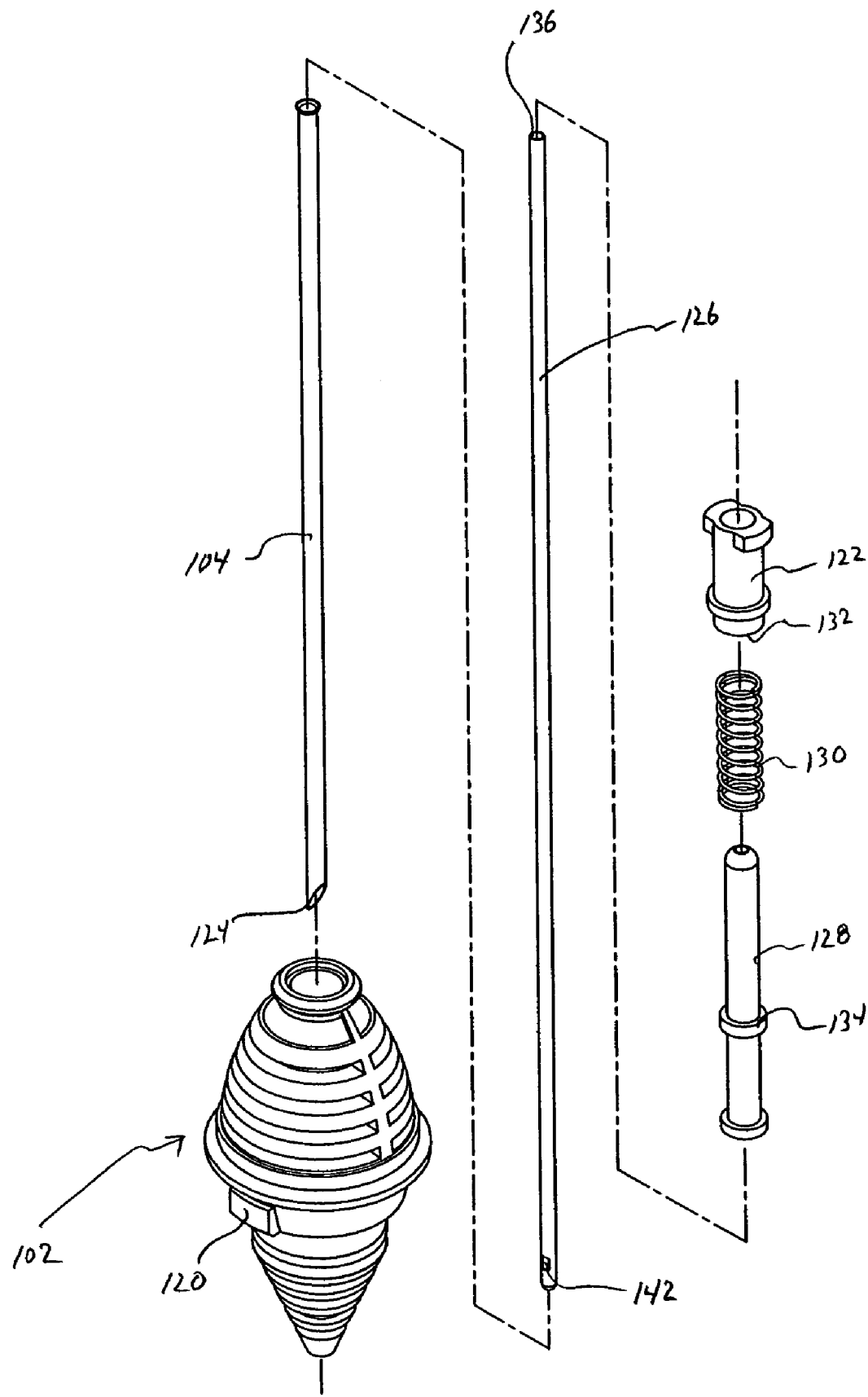
FIG. 6 is a perspective view with parts separated of the insufflation instrument in accordance with the embodiment of FIGS. 1-5.
Figure 16:
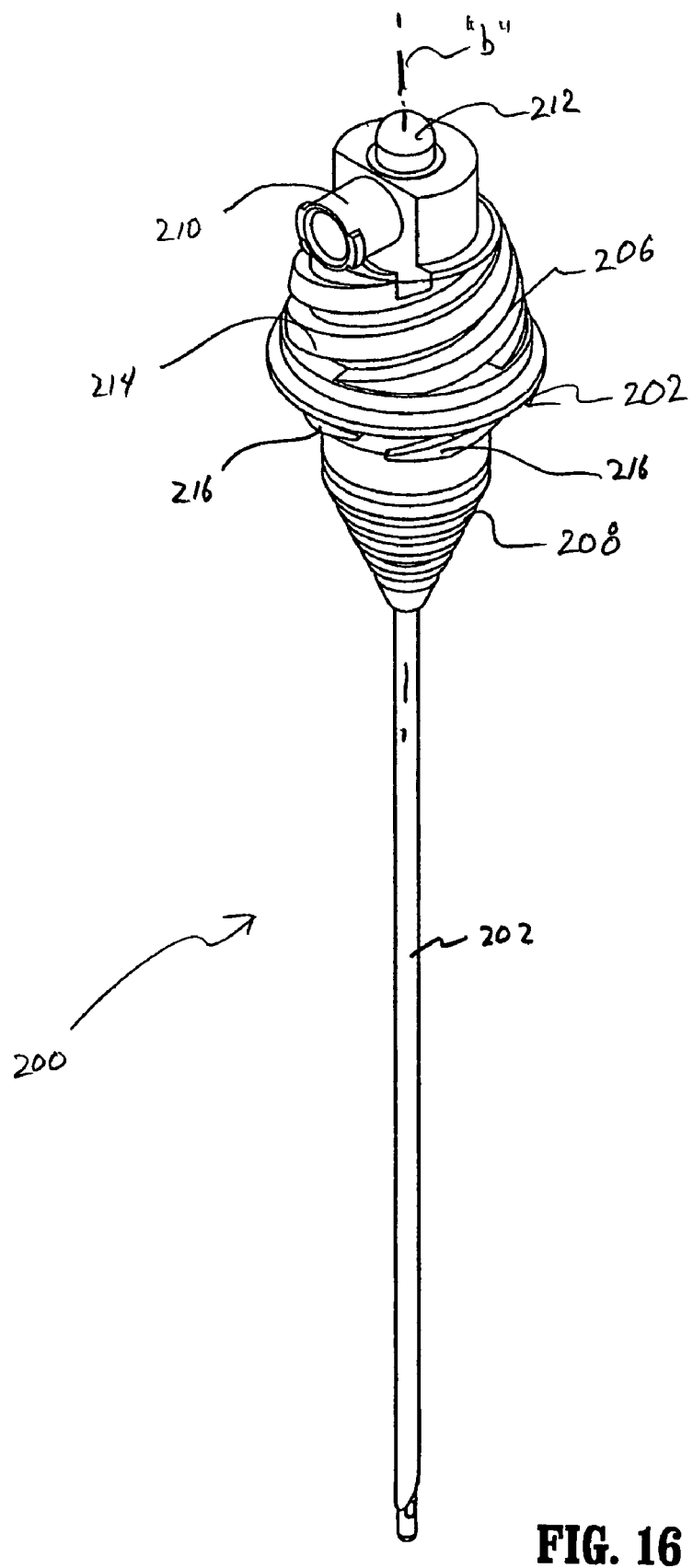
FIG. 16 is a perspective view of an alternate embodiment of an insufflation instrument in accordance with the present disclosure.
Figure 17:
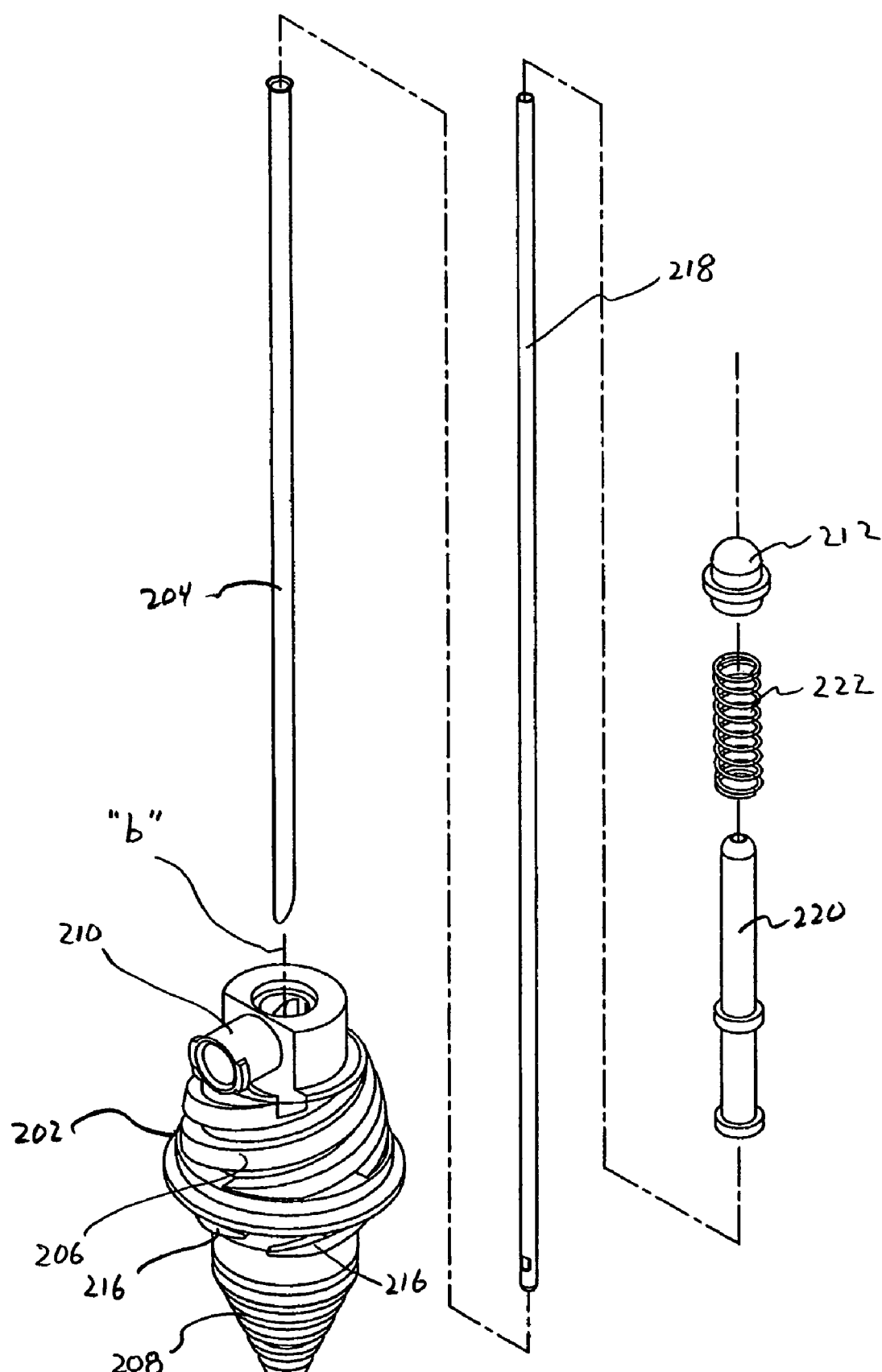
FIG. 17 is a perspective view with parts separated of the insufflation instrument in accordance with the embodiment of FIG. 16.

Housing 102 generally defines an oval or egg shape. The external surface of housing 102 includes peripheral ribs 118 disposed on each of housing components 106, 108. Ribs 118 are advantageously dimensioned to enhance gripping engagement by the user and may comprise any shape, such as annular, as shown in FIG. 5, or helical, as shown in FIG. 16. As best depicted in FIGS. 6 and 7, housing 102 further includes a pair of diametrically opposed locking tabs 120 extending radially outwardly from the outer surface of first housing component 106 adjacent the midsection of the housing 102. Tabs 120 are received within gaps 44 of access housing 22 (FIG. 4) during assembly to secure or lock insufflation instrument 100 within access instrument 20. In particular, during the positioning of insufflation instrument 100 within access instrument 20, tabs 120 are aligned with gaps 44. Insufflation instrument 100 is then advanced within access instrument until tabs 120 clear shelves 40 of access housing 22, and the insufflation instrument is rotated to position tabs 120 beneath shelves 40 to secure the insufflation instrument 100 and access instrument 20 (see also FIG. 3). In an alternative arrangement, access housing 22 and housing 102 include cooperating helical threads.

Insufflation housing 102 further includes port 122 at a proximal end of housing 102 which connects to a supply of insufflation gas or gaseous media such as $CO_2$ gas as is known in the art. Port 122 may be secured to first housing component 106 by conventional means, such as adhesives or welding, and is preferably aligned with the longitudinal axis "a". Port 122 desirably comprises connector 123 and is preferably substantially transparent or translucent—to permit viewing by the surgeon into the interior of the port 122 the significance of which will be appreciated from the description provided hereinbelow. In this regard, port 122 and/or luer connector 123 may be fabricated from a molded clear polymeric material or glass.

Referring again to FIGS. 1-3, in the assembled condition, insufflation housing 102 of insufflation instrument 100 is secured within access housing 22 of access instrument 20 through the cooperation of tabs 120 of insufflation housing 102 and shelves 40 of access housing 22 as discussed hereinabove. Second housing component 108 resides within the proximal end of elongate member 24 of access instrument 20. The tapered configuration of second housing component 108 generally corresponds to the arrangement of elongate member 24 at its proximal end, and accordingly may provide support for the elongate member 24. Seal 36 within access housing 22 engages the outer surface of insufflation housing 102, specifically, first housing component 106, in fluid tight relation therewith, to prevent passage of gases through access instrument 20. This is best seen in FIG. 3. As also shown in FIG. 3, second housing component 108 supports the proximal end of the elongate member 24.

Referring now to FIGS. 5-8, insufflation sleeve 104 is securely mounted to second housing component 108 of insufflation housing 102 by conventional means. Insufflation sleeve 104 is generally tubular in shape and defines a sharpened distal end 124 (e.g., a beveled end) to assist in penetrating the body tissue. Insufflation sleeve 104 is rigid and may be made of titanium, stainless steel, a polymeric material, or any suitable bio-compatible material. Insufflation sleeve 104 has stylet 126 disposed within the interior of the sleeve 104. Stylet 126 has stylet housing 128 securely mounted in coaxial arrangement about the proximal end of the stylet 126. Stylet housing 128 has an annular wall 134 for engagement with coil spring 130 coaxially mounted about the stylet housing 128. Coil spring 130 engages, at its rear end, the distal end or annular wall 132 of port 122 and, at its forward end, the annular wall 134 of stylet housing 128. Stylet 126 and stylet housing 128 are adapted for reciprocal longitudinal movement from an extended position shown in FIG. 8 to a retracted position depicted in FIG. 9. With this arrangement, coil spring 130 normally biases stylet housing 128 and stylet 126 to its forward extended position depicted in FIG. 8.

Figure 9:
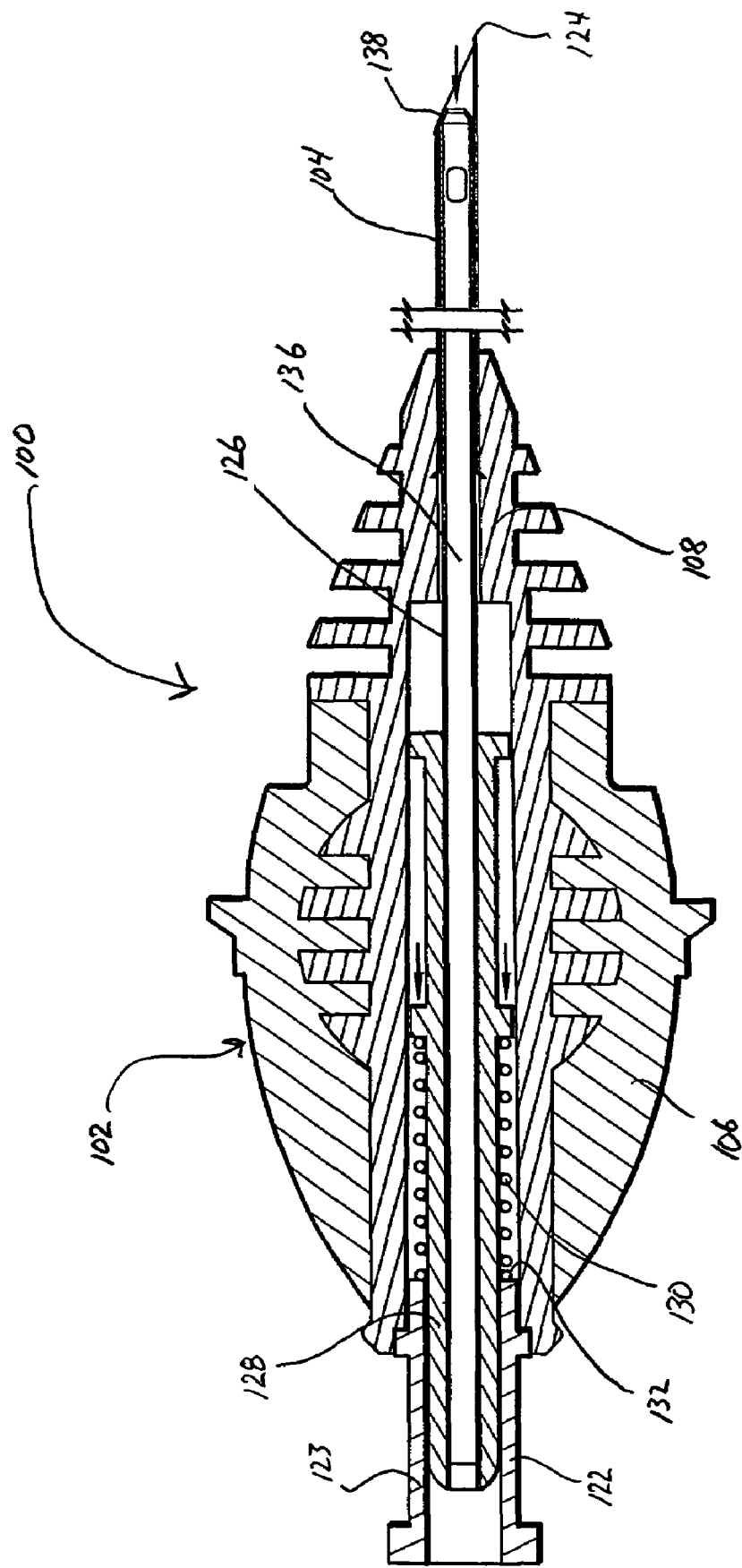
FIG. 9 is a side cross-sectional view similar to the view of FIG. 8 illustrating the stylet of the insufflation instrument in a retracted position.

Stylet 126 defines an internal axial lumen 136 which communicates with the lumen of port 122 to receive the gaseous media or fluids, e.g., $CO_2$ gas. Alternatively, stylet 126 may be devoid of a lumen whereby the insufflation gases pass through insufflation sleeve 104. Preferably, stylet 126 and stylet housing 128 are arranged with port 122 and dimensioned so as to be received in the port 122 upon movement from the extended position to the retracted position. The proximal ends of stylet 126 and stylet housing 128 preferably reside within port 122 and preferably traverse within the port 122 during rearward retracting movement of the stylet 126 as depicted in FIG. 9. In alternate embodiments, stylet housing 128 and stylet 126 comprise an integral, unitary part.

Referring now to FIGS. 10-11, stylet 126 further defines a rounded or generally blunt distal end 138 to prevent undesired penetration through tissue. Blunt end 138 defines at least one opening to supply insufflation gases to the body cavity. In the embodiment of FIGS. 10 and 11, stylet 126 has an axial opening 140 and a secondary opening 142 provided in the outer wall of stylet 126 and proximally disposed from axial opening 140.

In use, insufflation instrument 100 is positioned within access instrument 20 and secured within the access instrument 20 through the shelves and tabs 40, 120 arrangement in the aforedescribed manner. With reference to FIGS. 12-13, insufflation instrument 100 is then applied against the patient's abdominal area. Upon contacting the tissue with blunt end 138 of stylet 126, the stylet 126 retracts to the position depicted in FIG. 9 against the bias of coil spring 130 to expose sharpened end 124 of insufflation sleeve 104. At this point, the surgeon can confirm that stylet 126 is in the retracted position by viewing through port 122 to see that the proximal end of stylet housing 128 is within the interior of the port 122 as shown in FIG. 9. The proximal end of stylet housing 128 may be coated or colored, e.g., red, to facilitate visualization within port 122. As port 122 is disposed at the proximal end of housing 128, manipulation of the insufflation instrument 100 is generally not required to see the proximal end of the stylet 126 or stylet housing 128 to confirm that the stylet 126 is in a retracted position.

Figure 14:
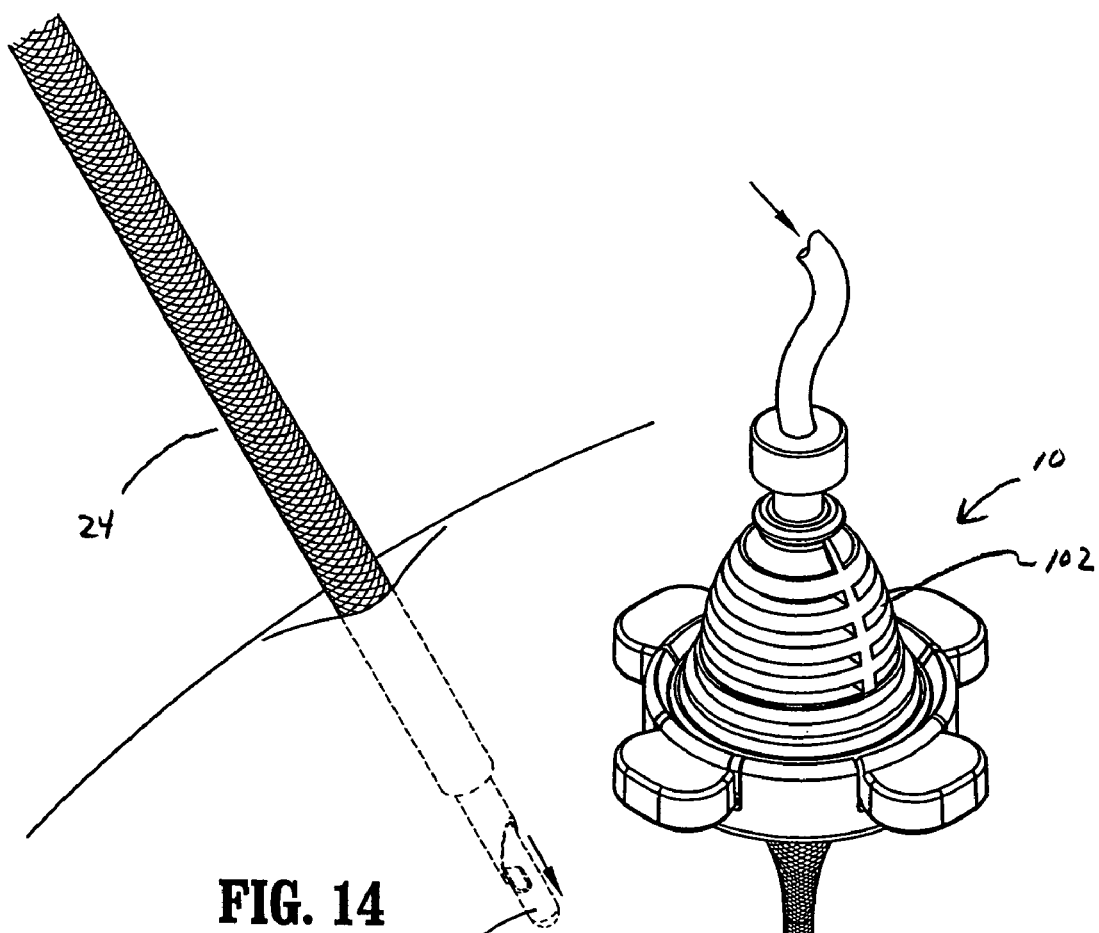
FIG. 14 is a perspective view illustrating the insufflation instrument and the access instrument accessing the underlying body cavity.
Figure 15:
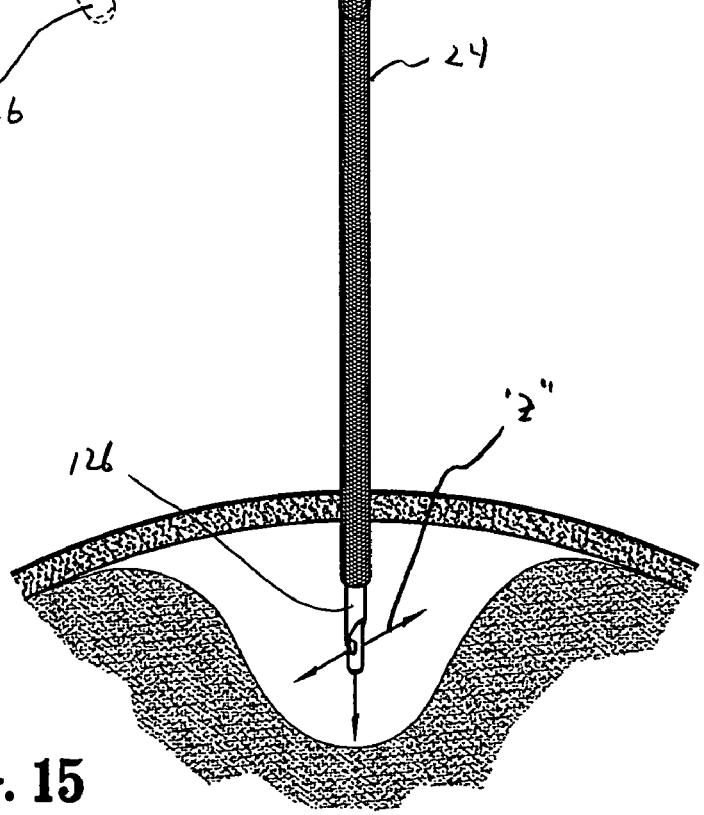
FIG. 15 is a perspective view illustrating use of the insufflation instrument to introduce fluids within the body cavity.

The procedure is continued by applying force to insufflation instrument 100 such that sharpened end 124 of insufflation sleeve 104 penetrates the tissue to enter the abdominal cavity. Once the cavity is accessed, stylet 126 is free to move forwardly to its extended position of FIG. 8 under the influence of coil spring 130. In this position, blunt end 138 of stylet 126 extends beyond sharpened end 124 of insufflation sleeve 104 to prevent puncture or laceration of internal abdominal structures as shown in FIG. 14. The gaseous supply is connected to port 122 to permit insufflation gases to flow as indicated by the directional arrows "z" through axial lumen 138 of stylet 126 and out openings 140, 142 to expand the peritoneal cavity as depicted in FIG. 15. Upon achieving the desired pressure, insufflation instrument 100 may be removed by rotating the instrument 100 to a position where diametrical tabs 120 are aligned with gaps 44 and the insufflation instrument 100 is removed leaving access instrument 20 within the abdominal cavity. Thereafter, access instrument 20 is utilized as a conduit for insertion of instruments, scopes, etc. to perform the desired surgical procedure. As noted, elongate member 24, preferably in the form of a tubular braid, of access instrument 20 may be expanded with a dilator to increase the size of lumen to permit introduction of larger-sized instruments.

Figure 18:
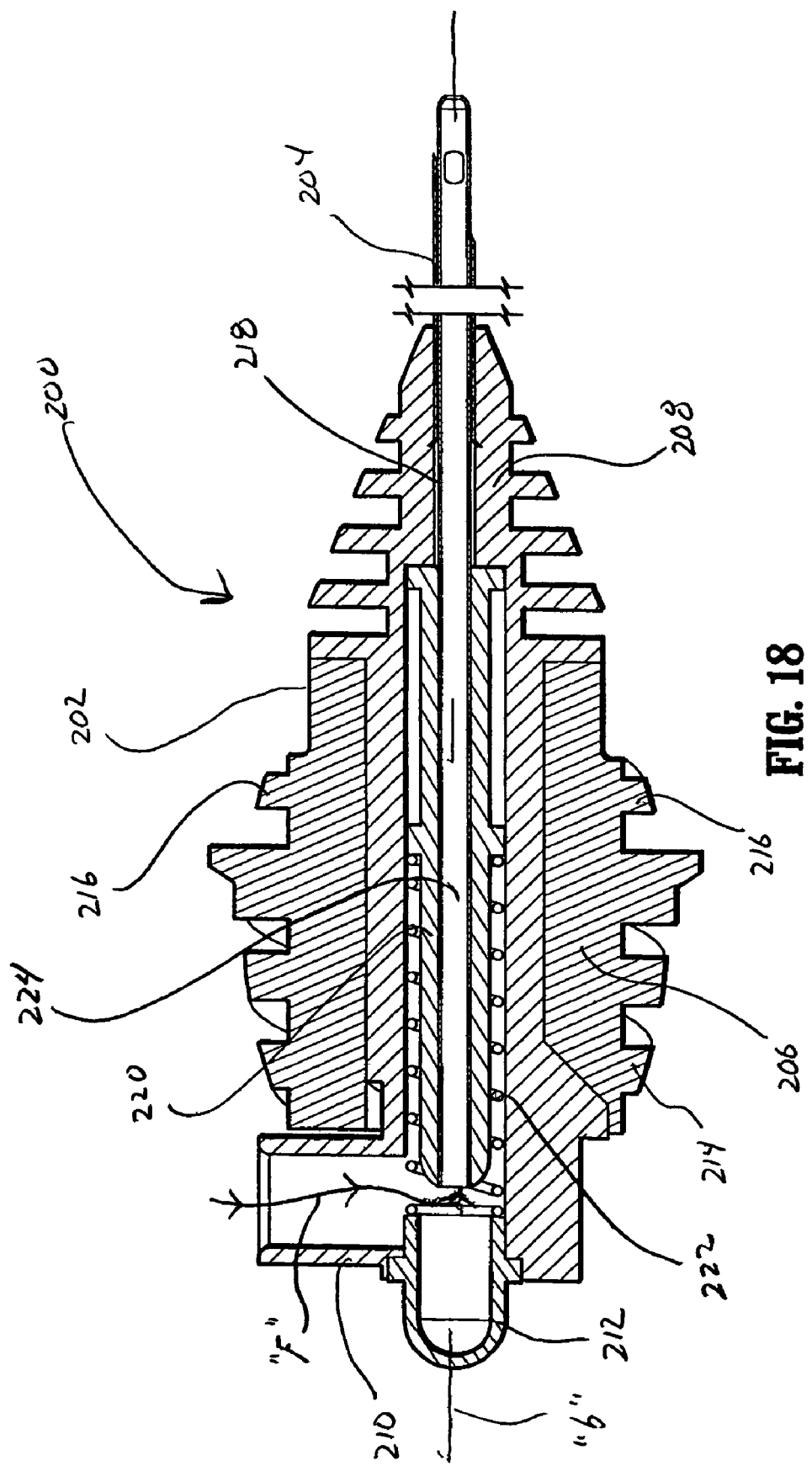
FIG. 18 is a side cross-sectional view of the insufflation instrument in accordance with the embodiment of FIGS. 16 and 17 illustrating the stylet in an extended position.

Referring now to FIGS. 16-20, there is illustrated an alternate embodiment of the insufflation instrument for use in the system 10 of the present disclosure. Insufflation instrument 200 includes housing 202 and insufflation needle 204 connected to and extending from the housing 202. Housing 202 includes first and second components 206, 208, as best seen in FIG. 18. Second component 208 extends at least partially within first component 206 and has port 210 integrally formed therewith. Port 210 extends from housing 202 in transverse relation with respect to the longitudinal axis "b" of insufflation instrument 200. Port 210 desirably includes a luer connector. An indicator bulb 212 is mounted to proximal end of housing 202 adjacent port 210. Indicator bulb 212 is preferably formed of a substantially transparent or translucent material such as glass or plastic. The first component and second component 206, 208 may be secured to one another in a snap fit arrangement, or first component 206 may be molded onto second component.

First component 206 includes annular ribs 214 which are helical in configuration to facilitate gripping engagement by the user. First component 206 also includes external thread portions 216 which replace tabs 120 of the embodiment of FIG. 1. Threads 216 cooperate with internal ribs or threads 80 (FIG. 20) defined with access housing 22 to secure insufflation instrument 200 relative to access instrument 20. In particular, threads 216 are helical in configuration and are dimensioned to engage cam surfaces 82 of internal ribs 80 during rotation of insertion instrument 200 to thereby cause the instrument 200 to advance within access instrument 20 until the threads 216 are secured beneath the ribs 80. In this position of threads 216, insufflation instrument 200 is secured relative to access instrument 20.

Insufflation instrument 200 further includes stylet 218 disposed within insufflation needle 204 and stylet housing 220 mounted to the proximal end of the stylet 218. Stylet 218 is normally biased by coil spring 222 to the forward position depicted in FIG. 18. In this position, the proximal end of stylet 218 is spaced from indicator bulb 212, or is otherwise not visible through the indicator bulb 212. Preferably, the proximal end of the stylet 218 is spaced from indicator bulb 212, thereby defining a flow path for insufflation gases to enter the axial lumen 224 of the stylet 218 through port 210. This flow path is identified by indicator arrow "F". Upon contact of the distal end of stylet 218 with tissue, the stylet 218 retracts to the position depicted in FIG. 19. In this position, the proximal end of stylet 218 is received within indicator bulb 212 thereby terminating the flow path "F" through which the insufflation gases may pass. Thus, even if the gas supply is open, no insufflation gases will pass within the axial lumen 224 of stylet 218 in that the lumen 224 is sealed at its proximal end by features on the stylet 218 or stylet housing 228. It is envisioned that an internal or external O-ring may be provided along the inner surface of indicator bulb 212 or the outer surface of stylet housing 220. Alternatively, lubrication or close tolerances between bulb 212 and stylet housing 220 may be used to form a seal. In all other respects, stylet 218 operates in a similar manner to the stylet 126 of FIG. 1. As the indicator bulb 212 is disposed at the proximal end of the housing 202, it is not generally necessary to manipulate the instrument 200 in order to view the proximal end of the stylet or stylet housing and confirm that the stylet is retracted.

Figure 19:
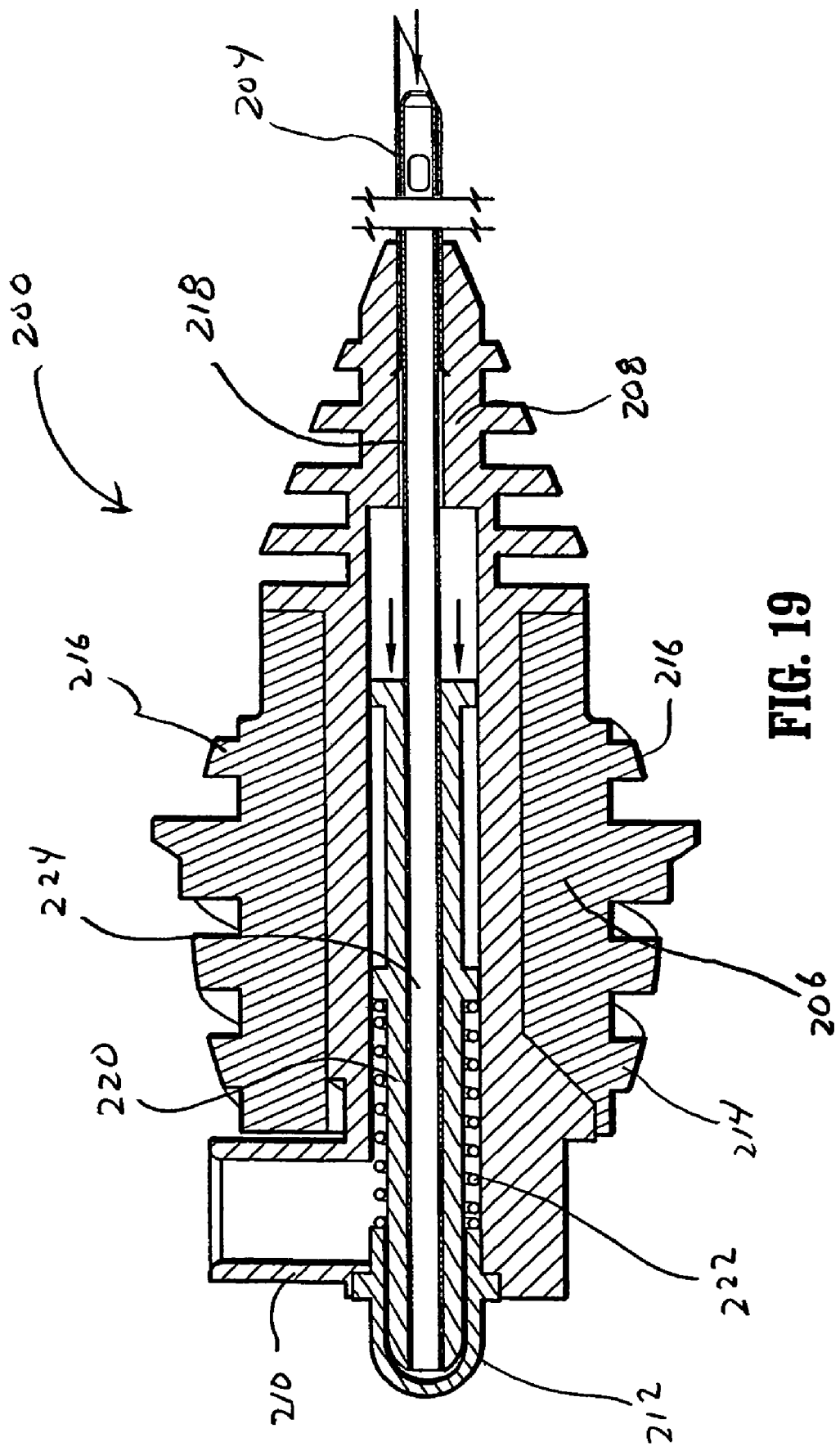
FIG. 19 is a side cross-sectioned view similar to the view of FIG. 18 illustrating the stylet in a retracted position.
Figure 20:
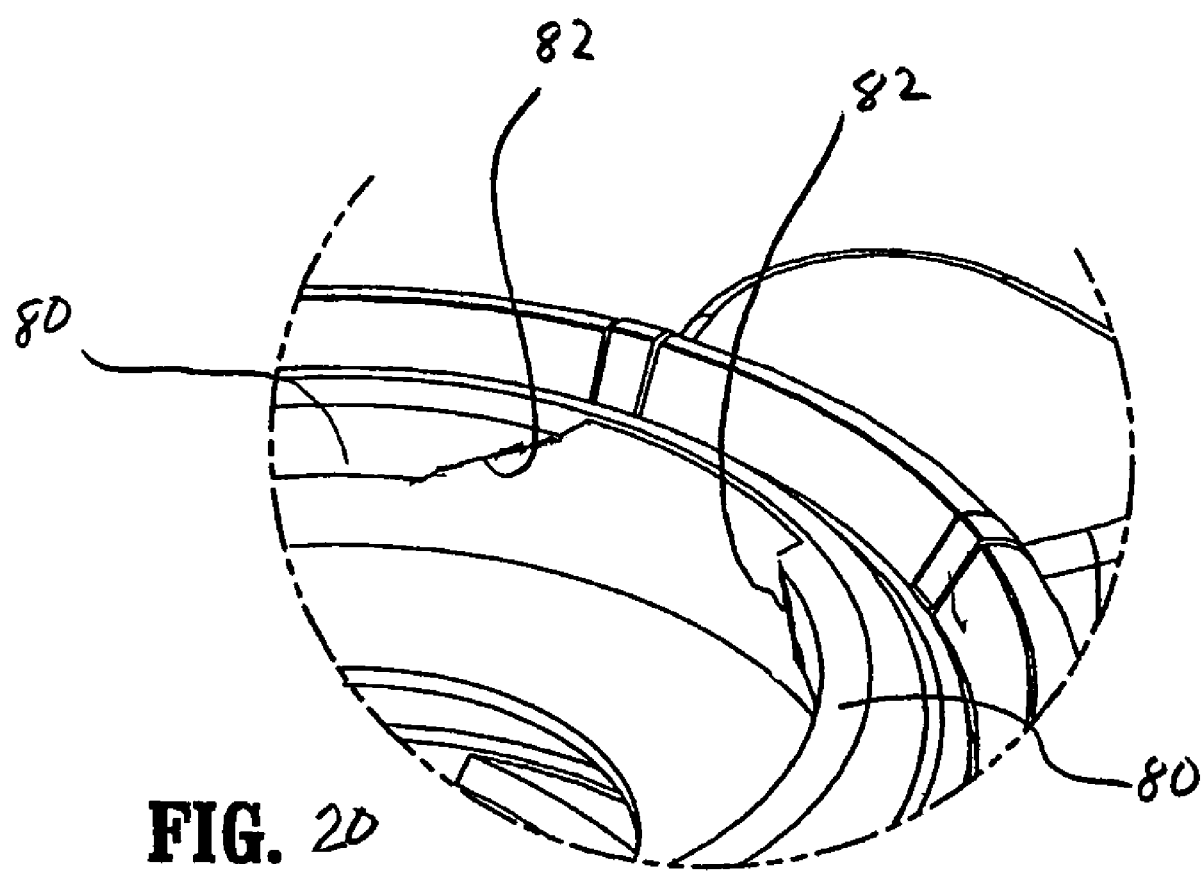
FIG. 20 is an enlarged isolated view of the access housing of the access instrument in accordance with the embodiment of FIGS. 16-19.

In further embodiments, luer connector 210 is disposed along the "b" axis, on top of housing 202 and the indicator may comprise a window on the side of housing 202. In another embodiment, indicator bulb 212 shown in FIG. 19 is eliminated and a window is provided on the side of housing 202. In each of these embodiments, the stylet or stylet housing preferably has a colored section arranged so as to be visible in the window when the distal end of the stylet is retracted from the sharpened tip of the needle.

Figure 21:
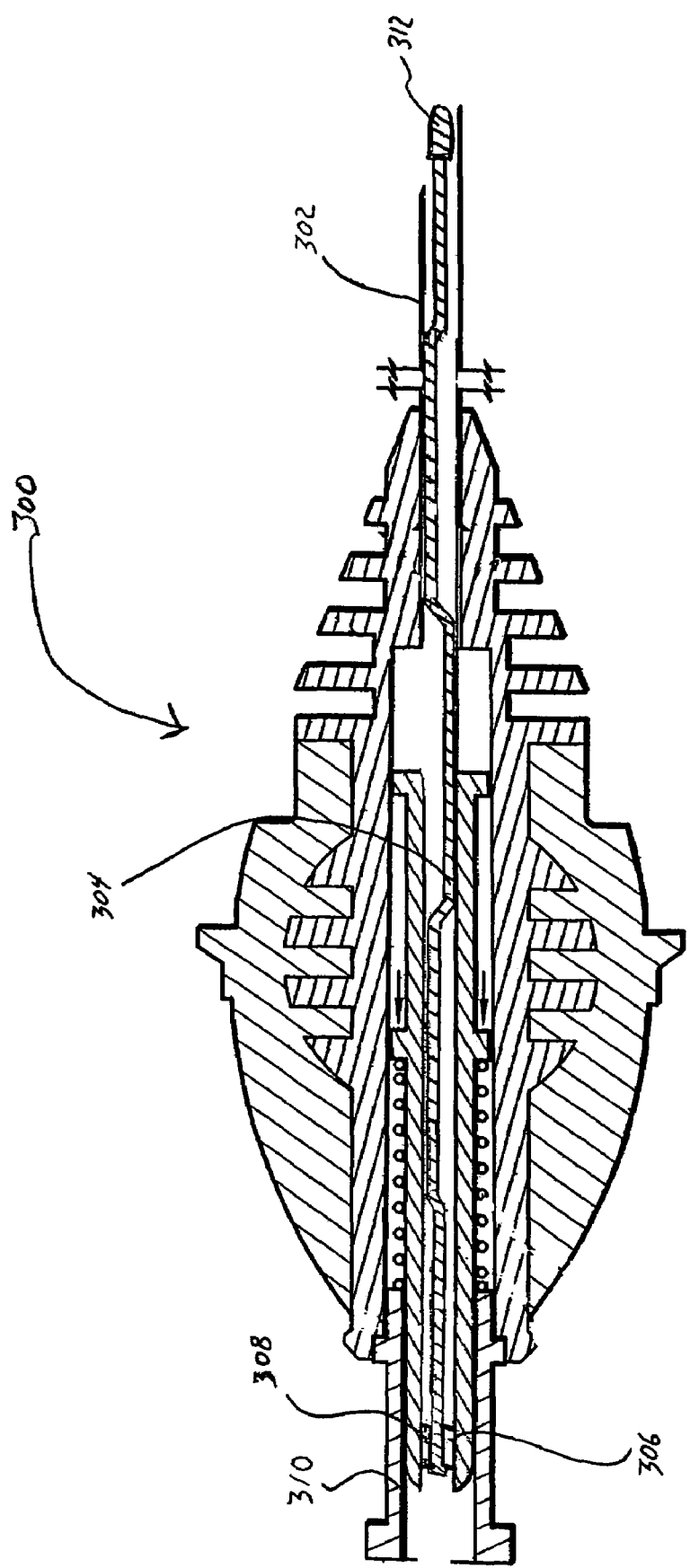
FIG. 21 is a side cross-sectional view of another alternate embodiment of an insufflation instrument in accordance with the present disclosure.

FIG. 21 illustrates another embodiment of the insufflation instrument of the present disclosure. In accordance with this embodiment, insufflation instrument 300 incorporates insufflation sleeve 302 and stylet 304 which is mounted for reciprocal movement within the sleeve 302 in the manner described in the prior embodiments. In FIG. 21, stylet 304 is shown in the retracted position. In a preferred embodiment, stylet 304 is secured, at its proximal end, within ferrule 306. Ferrule 306 is generally donut-shaped and is fixed within insufflation sleeve 302 through conventional means including adhesives, cements, etc. . . Ferrule 306 further defines one or more through bores 308 (shown in dashed lines) which permit the passage of insufflation gases from luer connector 310 and into insufflation sleeve 302. The distal end of stylet 304 defines blunt head 312 which engages the tissue. Insufflation instrument 300 is used in the same manner as the prior embodiments; however, the insufflation gases do not pass through a lumen of stylet 304 but pass from luer connector 310 through lumen 314 of insufflation sleeve 302 and into the body cavity.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. An insufflation apparatus, which comprises:
   an elongated sleeve defining a longitudinal axis and having a proximal end and a distal end, the distal end defining a sharpened tip;
   a housing having a proximal end and a distal end, the distal end being connected to the proximal end of the elongated sleeve, the housing defining a port for receipt of insufflation gases;
   a stylet disposed within the elongated sleeve and defining a passageway to direct the insufflation gases from the port into a body cavity, the stylet being movable between an extended position wherein the distal end of the stylet extends beyond the sharpened tip of the elongated sleeve and a retracted position wherein the distal end of the stylet is proximal of the sharpened tip of the elongated sleeve;
   a biasing member engagable with the stylet so as to bias the stylet toward the extended position; and
   an indicator bulb mounted to the proximal end of the housing and extending therefrom, the indicator bulb having a generally transparent wall portion whereby the proximal end of the stylet is visible through the indicator bulb when the stylet is in the retracted position.

2. The insufflation apparatus according to claim 1 wherein the port extends in transverse relation relative to the longitudinal axis of the elongated sleeve.

3. The insufflation apparatus according to claim 1 wherein the stylet defines an internal lumen, the internal lumen defining the passageway to permit passage of the insufflation gases therethrough and at least one opening to permit the insufflation gases to exit the internal lumen.

4. The insufflation apparatus according to claim 3 wherein the stylet includes an axial opening and a second opening spaced from the axial opening, the axial opening and the second opening adapted to permit the insufflation gases to exit the internal lumen of the stylet.

5. The insufflation apparatus according to claim 3 wherein the housing defines a flow path for the insufflation gases to flow through the port to the internal lumen of the stylet wherein the flow path is interrupted upon movement of the stylet to the retracted position to thereby prevent the insufflation gases from entering the internal lumen of the stylet.

6. The insufflation apparatus according to claim 5 wherein the port is disposed transversely with respect to the longitudinal axis of the elongated sleeve, the stylet being arranged within the passage so that, in the retracted position, the stylet blocks an opening within the port.

7. The insufflation apparatus according to claim 1 further including an access member dimensioned to access an underlying body cavity, the access member including a radially expandable sleeve, the elongated sleeve and the stylet being positionable within the access member.

8. The insufflation apparatus according to claim 7 including means for securing the access member relative to the elongated sleeve.

9. The insufflation apparatus according to claim 8 wherein the access member includes an access housing and an access sleeve.

10. The insufflation apparatus according to claim 9 wherein the means for securing includes corresponding thread members disposed on the access housing and the insufflation housing.

11. The insufflation apparatus according to claim 9 wherein the means for securing includes a locking shelf and locking tab mechanism associated with the access housing and the insufflation housing.

12. An insufflation apparatus, which comprises:
    a housing having a proximal end, a distal end and an insufflation port for connection to a supply of insufflation gases;
    an elongated sleeve conducted to the housing and extending distally therefrom, the elongated sleeve having a penetrating tip;
    a stylet disposed within the sleeve, the stylet being movable from an extended position to a retracted position to expose the penetrating tip of the elongated sleeve;
    one of the elongated sleeve and the stylet defining a passageway for passage of insufflation gases from the port into a body cavity; and
    an indicator bulb mounted to the proximal end of the housing and extending therefrom, the indicator bulb defining a generally transparent wall portion to permit visualization within an interior of the housing to confirm movement of the stylet to the retracted position.

13. An insufflation apparatus, which comprises:
    a housing having a proximal end and a distal end, and defining a longitudinal axis;

an elongated sleeve conducted to the housing and extending distally therefrom, the elongated sleeve having a penetrating tip;

a stylet disposed within the sleeve, the stylet being movable from an extended position to a retracted position to expose the penetrating tip of the elongated sleeve;

one of the elongated sleeve and the stylet defining a passageway for passage of insufflation gases from the port into a body cavity; and an indicator bulb mounted to the proximal end of the housing and extending therefrom, the indicator bulb defining a generally transparent wall portion; and an insufflation connector port mounted to the housing in general transverse relation to the longitudinal axis of the housing and being distal of the indicator bulb, the insufflation connector port adapted for connection to a supply of insufflation gases.

14. The insufflation apparatus according to claim 13 wherein the housing defines a flow path for the insufflation gases to flow through from the insufflation connector port to the passageway of the one of the elongated sleeve and the stylet wherein the flow path is interrupted upon movement of the stylet to the retracted position to thereby prevent the insufflation gases from entering the passageway.

15. The insufflation apparatus according to claim 13 wherein the insufflation connector port is generally perpendicular to the longitudinal axis of the housing.

* * * * *